(12) United States Patent
Chishti et al.

(10) Patent No.: US 6,210,162 B1
(45) Date of Patent: Apr. 3, 2001

(54) CREATING A POSITIVE MOLD OF A PATIENT'S DENTITION FOR USE IN FORMING AN ORTHODONTIC APPLIANCE

(75) Inventors: Muhammad Chishti, Menlo Park; Huafeng Wen, Redwood Shores, both of CA (US)

(73) Assignee: Align Technology, Inc., Sunnyvale, CA (US)

( * ) Notice: Subject to any disclaimer, the term of this patent is extended or adjusted under 35 U.S.C. 154(b) by 0 days.

(21) Appl. No.: 09/311,715

(22) Filed: May 14, 1999

Related U.S. Application Data (60) Provisional application No. 60/050,342, filed on Jun. 20, 1997.

(51) Int. Cl.⁷ .................................................. A61C 11/00
(52) U.S. Cl. ............................................. 433/213; 433/24
(58) Field of Search ........................................ 433/24, 213

(56) References Cited

U.S. PATENT DOCUMENTS

| | | | |
|---|---|---|---|
| 3,660,900 | * | 5/1972 | Andrews .................................. 433/24 |
| 3,860,803 | * | 1/1975 | Levine ................................. 235/151.1 |
| 4,324,546 | * | 4/1982 | Heitlinger et al. ...................... 433/25 |
| 4,755,139 | * | 7/1988 | Abbatte et al. ........................... 433/6 |
| 4,798,534 | * | 1/1989 | Breads ...................................... 433/6 |
| 4,856,991 | * | 8/1989 | Breads et al. ............................. 433/6 |
| 4,936,862 | * | 6/1990 | Walker et al. .......................... 623/23 |
| 5,011,405 | * | 4/1991 | Lemchen ................................ 433/24 |
| 5,035,613 | * | 7/1991 | Breads et al. ............................. 433/6 |
| 5,055,039 | * | 10/1991 | Abbate et al. ......................... 433/24 |
| 5,059,118 | * | 10/1991 | Breads et al. ............................. 433/6 |
| 5,139,429 | * | 8/1992 | Andreiko et al. ...................... 433/24 |
| 5,186,623 | * | 2/1993 | Breads et al. ............................. 433/6 |
| 5,273,429 | * | 12/1993 | Rekow ................................. 433/215 |
| 5,338,198 | * | 8/1994 | Wu et al. .............................. 433/213 |
| 5,340,309 | * | 8/1994 | Robertson ............................. 433/69 |
| 5,342,202 | * | 8/1994 | Deshayes ............................. 434/270 |
| 5,368,478 | * | 11/1994 | Andreiko et al. ...................... 433/24 |
| 5,382,164 | * | 1/1995 | Stern ................................... 433/223 |
| 5,395,238 | * | 3/1995 | Andreiko et al. ...................... 433/24 |
| 5,431,562 | * | 7/1995 | Andreiko et al. ...................... 433/24 |
| 5,447,432 | * | 9/1995 | Andreiko et al. ...................... 433/24 |
| 5,452,219 | * | 9/1995 | Dehoff et al. ..................... 364/474.05 |
| 5,454,717 | * | 10/1995 | Andreiko et al. ...................... 433/24 |
| 5,474,448 | * | 12/1995 | Andreiko et al. ...................... 433/24 |
| 5,533,895 | * | 7/1996 | Andreiko et al. ...................... 433/24 |
| 5,549,476 | * | 8/1996 | Stern ................................... 433/223 |
| 5,587,912 | * | 12/1996 | Anderson et al. ................... 364/468 |
| 5,605,459 | * | 2/1997 | Kuroda et al. ....................... 433/214 |
| 5,607,305 | * | 3/1997 | Anderson et al. ................... 433/223 |
| 5,621,648 | * | 4/1997 | Crump ................................. 364/468 |
| 5,645,421 | * | 7/1997 | Slootsky ................................. 433/6 |

OTHER PUBLICATIONS

Biostar Operation & Training Manual, Great Lakes Orthodontics, Ltd. 20 pgs.*

Chiappone, "Constructing the Gnathologic Setup and Positioner", J. Clin. Orhod. vol. 14, No. 2., Feb. 1980, pp. 121–133.*

Cottnhgam, "Gnatologic Clear Plastic Positioner", Am. J. Orthod. vol. 55, No. 1, Jan. 1969, pp. 23–31.*

(List continued on next page.)

Primary Examiner—John J. Wilson
(74) Attorney, Agent, or Firm—Fish & Richardson PC (57) ABSTRACT

A positive mold for use in creating an orthodontic appliance is produced by obtaining a digital dentition model, such as a 3D geometric surface model or a 3D volumetric image model, that defines the shape of an orthodontic appliance and then altering the digital dentition model to remove a portion that does not affect the shape of the orthodontic appliance. The altered digital dentition model then is used to construct a positive mold for the orthodontic appliance. Processing circuitry, such as a programmed computer, is used to obtain and alter the digital dentition model. A rapid prototyping device, such as a stereolithography machine, is commonly used to construct the positive mold.

55 Claims, 6 Drawing Sheets

OTHER PUBLICATIONS

Cureton, "Correcting Maligned Mandadibular Incisors with Removable Retainers", J. Clin. Orthod. vol. 30, No. 7, Jul. 1996, pp. 390–395.*

Elsasser, Some Observations on the History and Uses of the Kesling Positioner, Am. J. Orthod. vol. 36, Jan.–Dec. 1950, pp. 386–374.*

Kamada et al., "construction of Tooth Positioners with LTV Vinyl Silicone Rubber and some case Reports", J. Nihon University School of Dentistry, vol. 24, No. 1, Mar. 1982, pp. 1–27.*

Kesling, The Philosophy of the Tooth Positioning Appliance, Am. J. Orthod. Oral surg. vol. 31, No. 6, Jun. 1945, pp. 297–304.*

Kesling, Coordinating the Predetermined Pattern and Tooth Positioner with Conventional Treatment, Am. J. Orthod. Oral. Surg. vol. 32, No. 5, May 1946.*

Kleeman et al., The Speed Positioner, J. Clin. Orthod. vol. 30, No. 12, Dec. 1996, pp. 673–680.*

Kuroda et al., Three dimensional Dental Cast Analyzing system Using Laser Scanning, Am. J. Ortho. Dentofac. Orthop, vol. 110, No. 4, Oct. 1996, pp. 365–369.*

Nishiyama et al., A New Construction of Tooth Positioner by LTV Vinyl Silicone Rubber, J. Nihon Univ. School of Dentistry, vol. 19, No. 2, Jun. 1977, pp. 93–102.*

Yoshii, Research on a New Orthodontic Appliance: The Dynamic Positioner (D.P.)–I. The D.P. concept and Implementation of Transparent Silicone Resin (Orthocon), Nippon Dental Review, vol. 452, Jun. 1980, pp. 61–74.*

Yoshii, "Research on A New Orthodontic Appliance: The Dynamic Positioner (D.P.)–II. Th D.P. Manufacturing Procedure and Clinical Applications", Nippon Dental Review, vol. 454, Aug. 1980, pp. 107–130.*

Yoshii, Research on a New Orthodontic Appliance: The Dynamic Positioner (D.P.)–III. The General concept of the D.P. Method and its Therapeutic Effect, Part 1. Dental and Functional Reversed Occlusion Case Reports, Nippon Dental Review, vol. 457, Nov. 1980, pp. 146–164.*

Yoshii, Research on a New Orthodontic Appliance: The Dynamic Positioner (D.P.)–III. The General concept of the D.P. Method and its Therapeutic Effect, Part 2. Skeletal Reversed Occlusion Case Reports, Nippon Dental Review, vol. 458, Dec. 1980, pp. 112–129.*

Sheridan, Moving Teeth with Essix™ Appliances: Windows & Divots™, Essix™ Appliences Fabrication, Application and Rationale, Raintree Essix & ARS Materials, Inc. Technical Magazine, www.essix.com/magazine/default, Aug. 1997, 7 pgs.*

Shilliday, Minimizing Finishing Problems with the Mini–positioner, Am.J. Orthod. vol. 59, No. 6 Jun. 1971, pp. 596–599.*

Warunek et al. Physical and Mechanical Properties of Elastomers in Orthodontic Positioners, Am. J. Orhtod. Dentofac. Orthop, vol. 95, No. 5, May 1989, pp. 388–400.*

Wells, Application of the Positioner Appliance in Orthodontic Treatment, Am. J. Orthodont. vol. 58, No. 4, Oct. 1970, pp. 351–366.*

* cited by examiner

CREATING A POSITIVE MOLD OF A PATIENT'S DENTITION FOR USE IN FORMING AN ORTHODONTIC APPLIANCE

RELATED APPLICATIONS

This application is related to U.S. patent application 09/169,276, filed on Oct. 8, 1998, and entitled "Computer Automated Development of an Orthodontic Treatment Plan and Appliance," which claims priority from PCT application PCT/US98/12681, filed on Jun. 19, 1998, and entitled "Method and System for Incrementally Moving Teeth", which claims priority from U.S. patent application Ser. No. 08/947,080, filed on Oct. 8, 1997, which claims priority from U.S. provisional application No. 60/050,342, filed on Jun. 20, 1997, all of which are incorporated by reference into this application.

This application also is related to copending U.S. patent application Ser. Nos. 09/169,034, filed on Oct. 8, 1998, and entitled "Defining Tooth-Moving Appliances Computationally"; 09/169,036, filed on Oct. 8, 1998, and entitled "System and Method for Positioning Teeth"; 09/264,547, filed on Mar. 8, 1999, and entitled "Segmenting a Digital Dentition Model"; 09/311,941, filed on May 14, 1999, and entitled "Manipulating a Digital Dentition Model to Form Models of Individual Dentition Components"; and 09/311,716, filed on May 14, 1999, and entitled "Digitally Modeling the Deformation of Gingival Tissue During The Course of Orthodontic Treatment"; all of which are incorporated by reference.

TECHNOLOGICAL FIELD

The invention relates generally to the fields of dentistry and orthodontics.

BACKGROUND

Two-dimensional (2D) and three-dimensional (3D) digital image technology has recently been tapped as a tool to assist in dental and orthodontic treatment. Many treatment providers use some form of digital image technology to study the dentitions of patients. U.S. patent application Ser. No. 09/169,276 describes the use of 2D and 3D image data in forming a digital model of a patient's dentition, including models of individual dentition components. That application also describes using the digital dentition models in developing an orthodontic treatment plan for the patient, as well as in creating one or more orthodontic appliances to implement the treatment plan.

Some of these orthodontic appliances are rigid, shell-like devices that fit over the patient's teeth, applying the forces necessary to move the teeth to prescribed final positions. Such an appliance can be produced by pressure forming a sheet of material around a positive mold. In general, the positive mold is a solid block manufactured from a resin-based material in a rapid prototyping process.

SUMMARY

The invention provides techniques for reducing the time and costs associated with producing positive molds for orthodontic appliances. Conventional techniques involve the use of digital models that generate solid molds, in most cases leading to the use of material in areas that have no effect on the shapes of the orthodontic appliances. In most instances, the techniques described here yield hollow, shell-like molds that use just enough material to withstand the appliance fabrication process. These molds do not include any material in many or most of the areas that do not affect the shape of the orthodontic appliance. As a result, mold fabrication is quicker and less expensive because less material is used for each mold.

One technique for producing a positive mold involves obtaining a digital dentition model, such as a 3D geometric surface model or a 3D volumetric image model, that defines the shape of an orthodontic appliance; altering the digital dentition model to remove a portion that does not affect the shape of the orthodontic appliance; and then using the altered digital dentition model to construct the positive mold. Processing circuitry, such as a programmed computer, is used to obtain and alter the digital dentition model. A rapid prototyping device, such as a stereolithography machine, is commonly used to construct the positive mold.

In some of the implementations in which a 3D geometric surface model of the dentition is used, altering the model involves creating another 3D surface model that is smaller than the 3D surface model of the dentition and defining a cutting surface that intersects both the 3D surface model of the dentition and the smaller 3D surface model. A cut operation is performed along the cutting surface to form a single 3D surface model that follows contours of both the 3D surface model of the dentition and the smaller 3D surface model. The single 3D surface model forms a shell having an outer surface that follows contours of the 3D surface model of the dentition and an inner surface that follows contours of the smaller 3D surface model. One technique for creating the smaller 3D surface model involves identifying an area that defines a cavity in the shell and forming the smaller 3D surface around the cavity.

In some implementations, the processing circuitry receives a 3D surface model of the dentition and creates a volumetric image model from the 3D surface model. One technique for doing so involves removing an outer layer of volume elements from the volumetric image model, such as by altering the image values assigned to the volume elements in the outer layer. The smaller 3D surface model can then be produced by forming a 3D surface around the volumetric image model after removing the outer layer of volume elements Another technique for creating the smaller 3D surface involves creating a copy of the 3D surface model of the dentition and reducing the size of the copy. One way to reduce the size of the model is to select points on the model and move the points toward an inner portion of the model. In some implementations, each of the points is a vertex on a 3D surface triangle, and moving the points involves, for each point, calculating normals for the triangles that share the point, averaging the normals to create an averaged normal, and moving the point along the averaged normal. Mathematical springs can be placed between adjacent pairs of the points to ensure that the triangle edges do not cross or buckle when the points are moved.

Other embodiments and advantages are apparent from the detailed description and the claims below.

DETAILED DESCRIPTION

U.S. patent application Ser. Nos. 09/169,276, 09/264,547, and 09/311,941, incorporated by reference above, describe techniques for generating a 3D digital data set that models individual components of a patient's dentition, including individual teeth and gingival tissue surrounding the teeth. One technique for forming the data set includes embedding a physical model of the patient's dentition in a potting material and optically scanning successive slices of the physical model with a destructive scanning system. This produces a three-dimensional (3D) volumetric image ("voxel representation") of the physical model. The physical model and the potting material usually have sharply contrasting colors, such as white and black, so that the volume elements ("voxels") in the voxel representation that correspond to the dentition model contrast sharply with the voxels that correspond to the background image.

The applications incorporated above also describe computer-implemented techniques for using the digital dentition model in designing and simulating an orthodontic treatment plan for the patient. One such technique involves receiving an initial data set that represents the patient's teeth before treatment, specifying a desired arrangement of the patient's teeth after treatment, and calculating the necessary translational and rotational forces that will move the teeth from the initial to the final positions. The initial data set often is the voxel representation obtained by optically scanning the physical dentition model. In some cases, the computer creates a 3D geometric surface model from the voxel representation and uses the surface model as the initial data set.

U.S. application Ser. Nos. 09/169,276 and 09/169,034 together describe techniques for designing and producing orthodontic appliances, such as polymer shell aligners, that carry out orthodontic treatment plans. Polymeric shell aligners and similar appliances are designed to fit over the patient's teeth and exert the forces required to move the teeth to the desired final positions. Polymeric shells are particularly useful because they are rigid enough and strong enough to carry out treatment, yet they are lightweight and, unlike conventional braces, are removable from the patient's mouth. Polymeric shells also are invisible or nearly invisible to the naked eye and therefore are more appealing to patients who consider traditional braces unsightly.

One technique for producing polymeric shell aligners or similar appliances involves creating a positive mold and then vacuum molding a sheet of material over the mold. The positive mold is usually formed by a rapid prototyping system, such as a stereolithography machine like the Model SLA-250/50 machine available from 3D System of Valencia, Calif. A rapid prototyping machine selectively hardens portions of a fluid, resin-based material and then separates the hardened material from the remaining unhardened material. The hardened material then serves as a positive mold for appliance fabrication. Each appliance is formed by placing the corresponding mold and a sheet of moldable material, such as thermal forming dental material available from Tru-Tain Plastics in Rochester, Minn., into a conventional pressure or vacuum molding machine and forcing the material to conform permanently to the shape of the mold. Suitable pressure molding and vacuum molding equipment is available from Great Lakes Orthodontics, Ltd., in Tonawanda, N.Y., and Raintree Essix, Inc.

Figure 1:
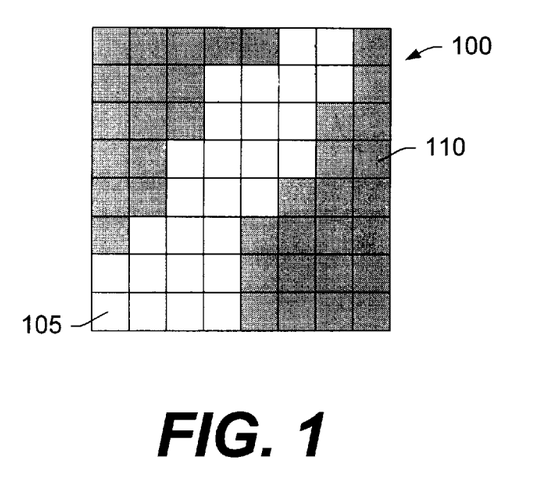
FIG. 1 is a cross sectional slice of a 3D volumetric digital model of a positive mold for use in producing an orthodontic appliance.

FIG. 1 shows a partial slice 100 taken from a digital image model (voxel representation) of a positive mold for use in appliance fabrication. Each image slice 100 in the voxel representation has a thickness of one voxel and includes both light-colored (e.g., white) voxels 105 and dark-colored (e.g., black) voxels 110. The light-colored voxels represent the positive mold, which in many cases replicates the patient's dentition at a selected treatment stage, and the dark-colored voxels represent the background image. A rapid prototyping machine analyzes each successive image slice 100 to identify the light-colored voxels and constructs the positive mold one layer at a time by hardening the fluid material at locations that correspond to the light-colored voxels.

Figure 2:
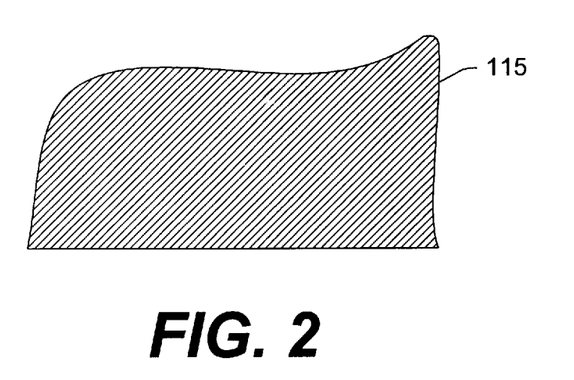
FIG. 2 is a cross sectional view of a solid mold for use in producing an orthodontic appliance.
Figure 3:
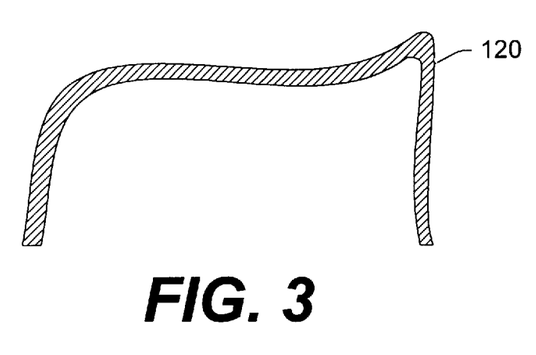
FIG. 3 is a cross sectional view of a hollow mold for use in producing an orthodontic appliance.

FIG. 2 shows a cross-section of a typical dentition mold 115 produced in a rapid prototyping process. The mold 115 is solid throughout. FIG. 3 shows a hollow mold 120, or hollow shell, that requires less material than the solid mold 115. The hollow mold 120 is lighter in weight than the solid mold 115, and the hollow mold 120 can be produced more quickly and less expensively than the solid mold 115.

Figure 4:
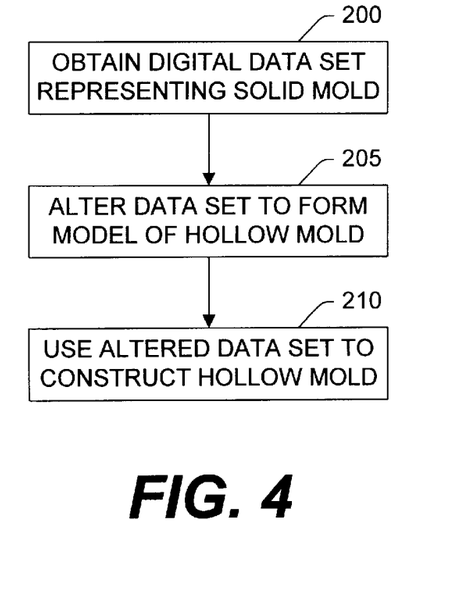
FIG. 4 is a flow chart of a technique for creating a digital model of the hollow mold of FIG. 3.
Figure 5:
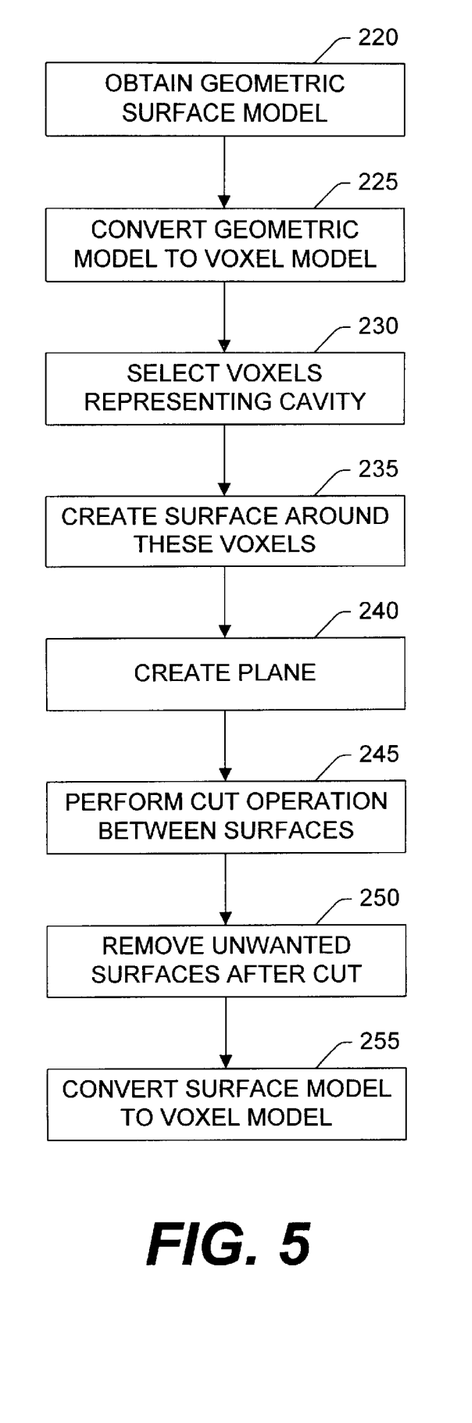
FIGS. 5, 6, 7, 8, 9, 10 and 11 illustrate one implementation of the technique of FIG. 4.

FIG. 4 illustrates a computer-implemented technique for producing hollow molds. The computer first receives or creates a digital data set embodying a 3D model of the solid mold (step 200). The computer then alters or removes a portion of the data set lying within the model of the solid mold to form a model of a hollow mold (step 205). The computer delivers the altered data set to a rapid prototyping device, such as a stereolithography machine, for use in constructing the hollow mold (step 210).

Figure 6:
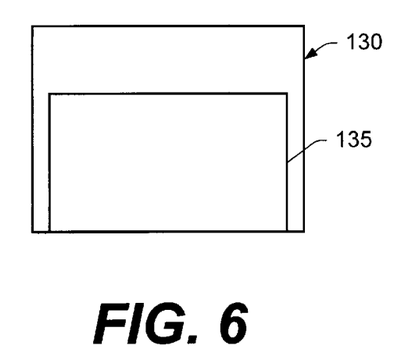
Figure 7:
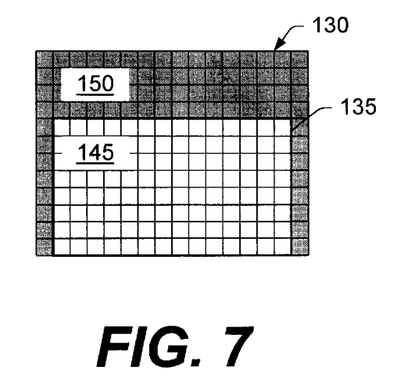

FIGS. 5 through 11 illustrate a specific implementation of this technique. The computer first receives the solid 3D digital model of the mold, which in this example is a 3D geometric surface model 135 (step 220). FIG. 6 shows a cross sectional slice 130 of the data set that includes a cross-section of the 3D geometric surface model 135. The computer then converts the 3D geometric surface model 135 into a 3D volumetric model ("voxel model") 140 of the solid mold (step 225). In alternative implementations, the computer receives a voxel model of the mold and therefore does need to create a voxel model from a geometric surface model. FIG. 7 shows a cross-sectional slice of the voxel model 140, in which light-colored voxels 145 represent the mold and dark-colored voxels 150 represent the background image. The light-colored voxels 145 are created to fit within the geometric surface model 135.

Figure 8:
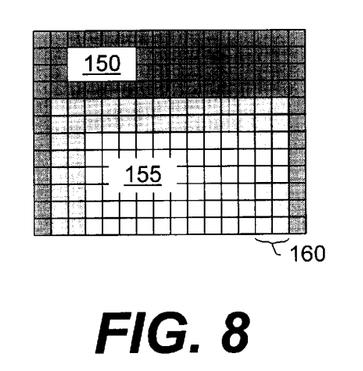

The computer then selects a group of voxels 155 that represent the hollow portion of the mold (step 230). As shown in FIG. 8, one way of doing this is by "removing" a layer of voxels 160 on the outer surface of the voxel model, e.g., by altering the image values of these voxels 160 to make the voxels 160 part of the background image. The thickness of the removed layer of voxels 160 defines the thickness of the hollow mold, or shell. The thicknesses of the molds often vary, but a shell thickness on the order of 0.5 mm is suitable in most instances. For a 3D volumetric model having voxels that are 0.05 mm cubes, removing a layer that is ten voxels thick produces a shell thickness of 0.5 mm. In many implementations, voxels in the data set used to generate the hollow mold are larger than voxels in the initial data set obtained by scanning a physical model of the patient's dentition. Creating larger voxels reduces the amount of data in the data set from which the mold is created and therefore reduces the amount of time and system resources required to process the data and create the hollow mold.

Figure 9:
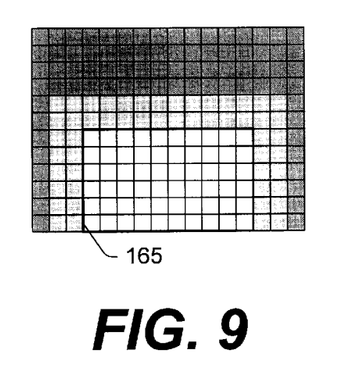
Figure 10:
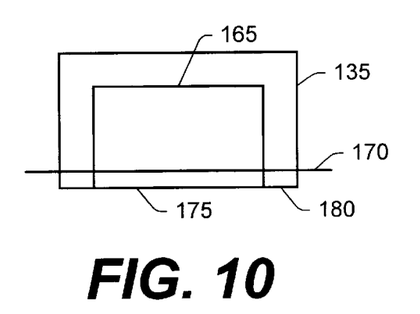
Figure 11:
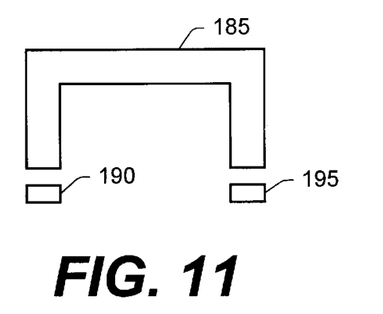
Figure 12:
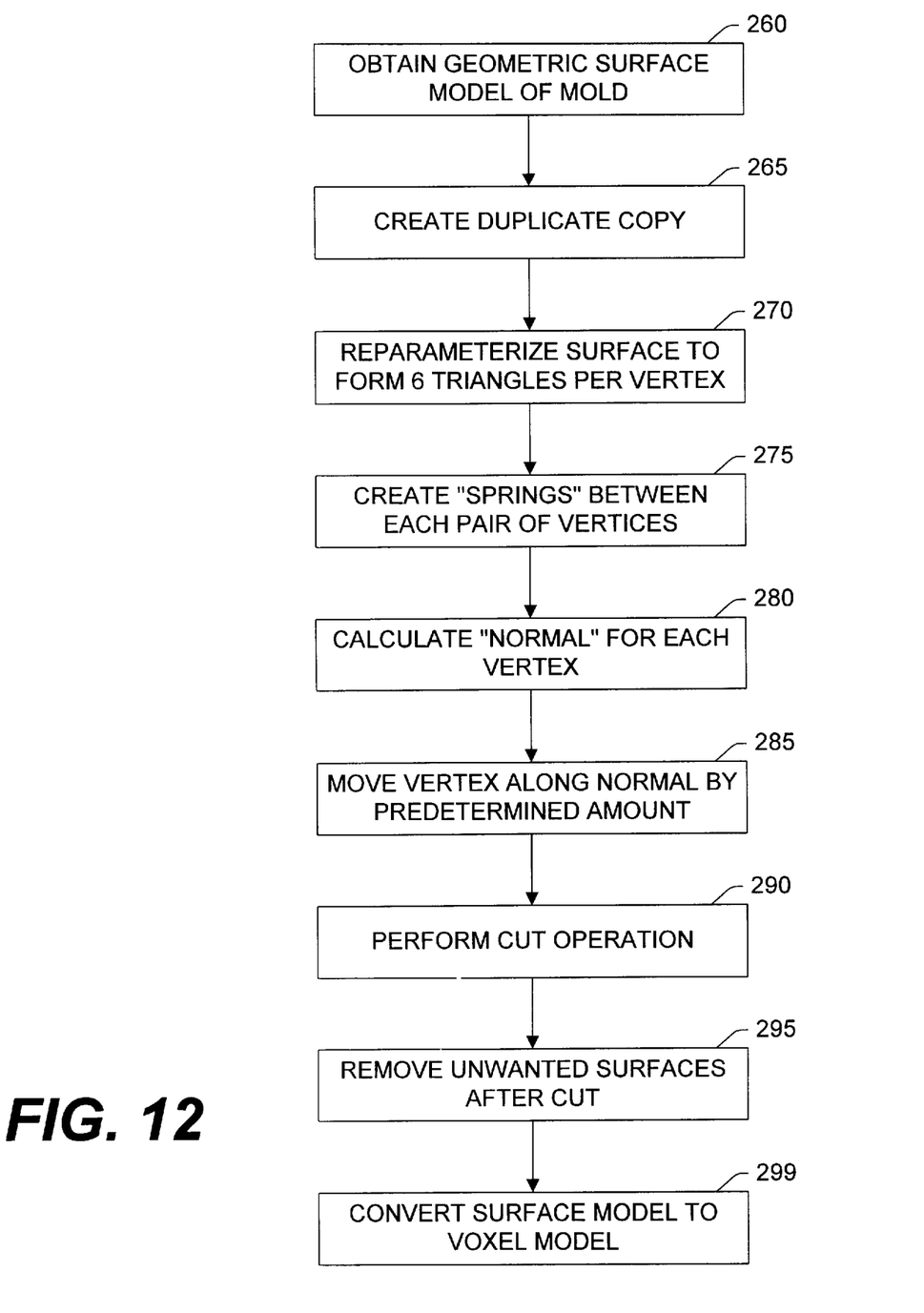
FIGS. 12, 13, 14, 15 and 16 illustrate another implementation of the technique of FIG. 4.

After removing the outer layer of voxels 160, the computer creates a geometric surface 165 around the group of voxels 155 that represent the hollow portion of the mold (step 235). This geometric surface forms a model of the void or cavity to be formed in the mold. FIG. 10 shows the relative size and position of the geometric surface model 165 of the cavity with respect to the geometric surface model 135 of the solid mold. The computer then creates a plane 170 that intersects both geometric surface models 135, 165 near their bottom surfaces 175, 180 (step 240) and performs a mathematical cut operation at the plane 170 (step 245). The resulting geometries include a geometric surface model 185 of the hollow mold and two geometric surfaces 190, 195 that have been severed from the hollow mold model 185. The computer discards the severed surfaces 190, 195 (step 250) and uses the remaining geometric surface model 185 to create the hollow mold. In most implementations, the computer converts the geometric surface model 185 into a voxel model before delivering the model to a rapid prototyping system (step 255). The distance between the cutting plane 170 and the bottom surfaces 175, 180 of the geometric models 135, 165 is usually on the order of two voxels (e.g., approximately 0.1 mm) so that only a very small portion of the model is discarded.

FIGS. 12 through 16 illustrate another implementation of the technique for producing the hollow mold 120. A computer applying this implementation begins by receiving a 3D geometric surface model of the solid mold (step 260) and creating a duplicate copy of the geometric surface model (step 265). This implementation allows the computer to operate directly on the geometric surface model, instead of on a voxel model as described above.

Figure 13:
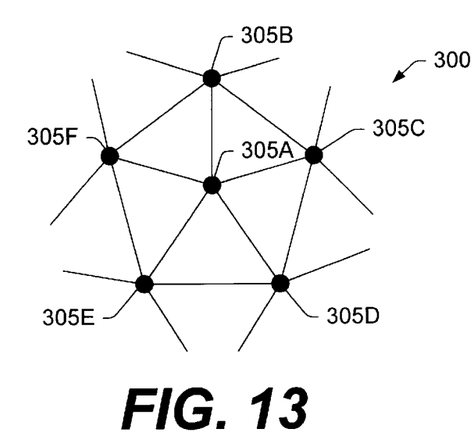
Figure 14:
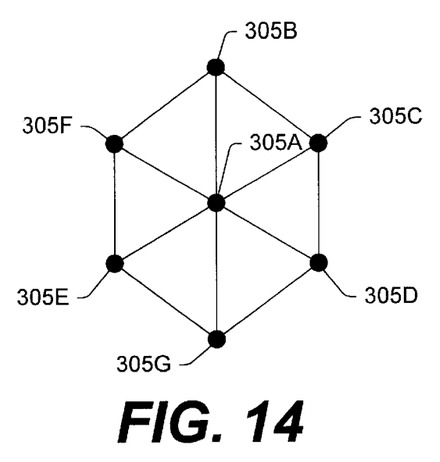
Figure 15:
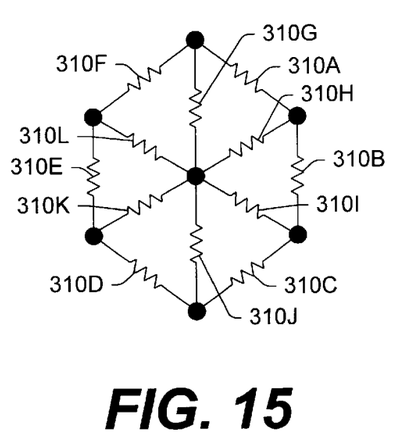
Figure 16:
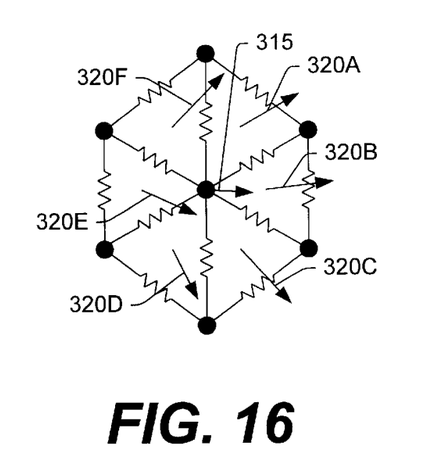

FIG. 13 shows a portion of the duplicate geometric surface model 300, which in most cases is a triangular surface mesh having many control points, or vertices 305A–F, shared by the triangles in the mesh. Each of the vertices 305A–F can be shared by virtually any number of triangles, although most are shared by only a few triangles, typically between three and seven triangles. For example, two of the vertices 305A, 305B shown in FIG. 13 are shared by five triangles and six triangles, respectively. The geometric surface model almost always includes vertices that are shared by differing numbers of triangles. For reasons that are discussed below, the computer in most cases reparameterizes the duplicate surface model 300 so that all or almost all of the vertices 305A–F in the model are shared by exactly six triangles (step 270). FIG. 14 shows an example in which the computer has moved two of the vertices 305D, 305E and has added a vertex 305G to ensure that six triangles share the center vertex 305A.

The computer then places mathematical "springs" 310A–L between each pair of adjacent vertices, along the edges of the triangles in the mesh (step 275). These springs 310A–L allow the computer to adjust the positions of the vertices 305A–G in a nonlinear manner, so that each of the vertices 305A–G can change positions without buckling or crossing the triangle edges. As a result, the computer can shrink the duplicate geometric surface model 300 without deforming or changing the shape of the model 300.

Before shrinking the model, the computer calculates a "normal" 315 for each vertex by calculating and then averaging the normals 320A–F of the six triangles that share the vertex (step 280). The computer then shrinks the model by moving each of the vertices 305A–G by a predetermined amount along the corresponding normal 315 (step 285). To create a hollow mold having a shell thickness of 0.5 mm, the computer moves each of the vertices 305A–G inward by approximately 0.5 mm. The computer creates a surface model of the hollow mold by defining a cutting plane, as described above, and performing a mathematical cut operation along the plane near the bottom surfaces of the original and duplicate geometric surface models (step 290). The computer then removes unwanted, severed surfaces from the model (step 295) and, in most cases, converts the geometric surface model of the hollow mold into a voxel model (step 299). Most rapid prototyping systems use the voxel model to construct the hollow mold.

Figure 17:
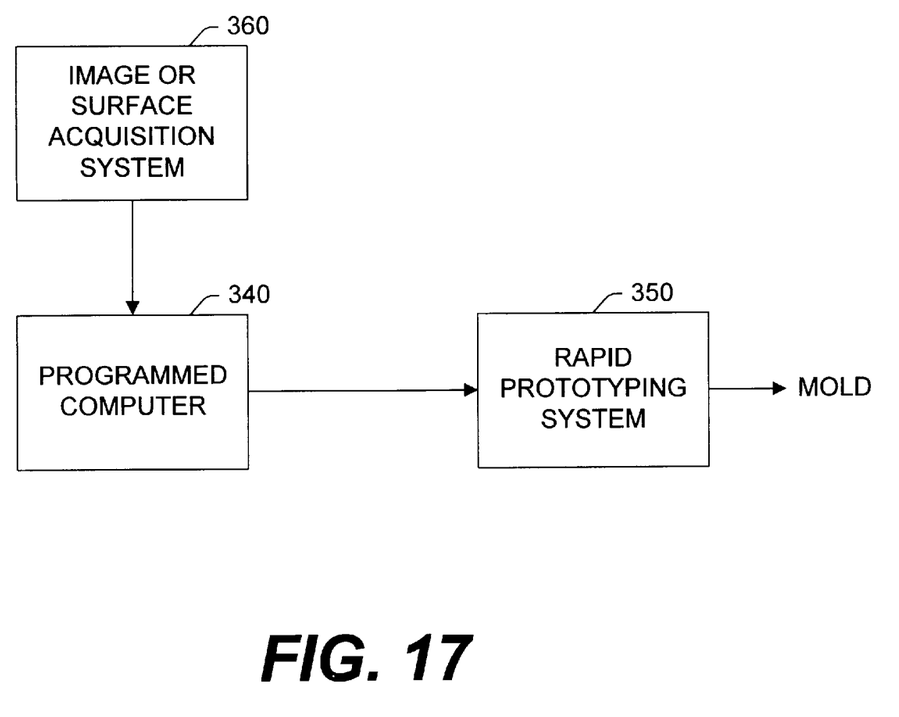
FIG. 17 shows a system used in producing positive molds for orthodontic appliances.

FIG. 17 shows a system used in producing positive molds for orthodontic appliances. The system includes a processing unit, such as a programmed computer 340, coupled to a mold producing system, such as a stereolithography machine or other rapid prototyping system 350. The computer 340 receives a digital dentition model, such as a 3D surface model or a volumetric image model, from an acquisition system 360, such as a laser scanning or destructive scanning device. The computer 340 manipulates the digital dentition model to form a digital model of the hollow mold, as described above, and then delivers the altered model to the rapid prototyping system.

Some implementations of the invention are realized in digital electronic circuitry, such as an application specific integrated circuit (ASIC); others are realized in computer hardware, firmware, and software, or in combinations of digital circuitry and computer components. The invention is usually embodied, at least in part, as a computer program tangibly stored in a machine-readable storage device for execution by a computer processor. In these situations, methods embodying the invention are performed when the processor executes instructions organized into program modules, operating on input data and generating output. Suitable processors include general and special purpose microprocessors, which generally receive instructions and data from read-only memory and/or random access memory devices. Storage devices that are suitable for tangibly embodying computer program instructions include all forms of non-volatile memory, including semiconductor memory devices, such as EPROM, EEPROM, and flash memory devices; magnetic disks such as internal hard disks and removable disks; magneto-optical disks; and CD-ROM.

The invention has been described in terms of particular embodiments. Other embodiments are within the scope of the following claims.

What is claimed is:

1. A method for use in producing a positive mold of an orthodontic appliance, the method comprising:

obtaining a digital dentition model that defines the shape of an orthodontic appliance;

altering the digital dentition model to remove a portion that does not affect the shape of the orthodontic appliance; and using the altered digital dentition model to construct a positive mold for the orthodontic appliance.

2. The method of claim 1, wherein using the altered digital dentition model to construct a positive mold for the orthodontic appliance includes delivering the altered digital dentition model to a rapid prototyping system.

3. The method of claim 2, wherein delivering the altered digital dentition model to a rapid prototyping system includes delivering a volumetric image model to a stereolithography machine.

4. The method of claim 2, wherein delivering the altered digital dentition model to a rapid prototyping system includes delivering data identifying boundaries of a surface model of the dentition.

5. The method of claim 1, wherein the digital dentition model includes a 3D surface model of a dentition, and wherein altering the digital dentition model includes:
creating another 3D surface model that is smaller than the 3D surface model of the dentition;
defining a cutting surface that intersects both the 3D surface model of the dentition and the smaller 3D surface model; and
performing a cut operation along the cutting surface to form a single 3D surface model that follows contours of both the 3D surface model of the dentition and the smaller 3D surface model.

6. The method of claim 5, wherein the single 3D surface model forms a shell having an outer surface that follows contours of the 3D surface model of the dentition and having an inner surface that follows contours of the smaller 3D surface model.

7. The method of claim 6, wherein creating the smaller 3D surface model includes:
identifying an area that defines a cavity in the shell; and
forming the smaller 3D surface around the cavity.

8. The method of claim 5, wherein using the altered digital dentition model to construct a positive mold for the orthodontic appliance includes delivering a data set that identifies boundaries of the single 3D surface model to a rapid prototyping system.

9. The method of claim 8, wherein delivering a data set to a rapid prototyping system includes delivering a volumetric image model of the single 3D surface model to a stereolithography machine.

10. The method of claim 5, further comprising creating a volumetric image model of the dentition from the 3D surface model of the dentition.

11. The method of claim 10, wherein creating the smaller 3D surface model includes removing an outer layer of volume elements from the volumetric image model.

12. The method of claim 11, wherein removing the outer layer of volume elements includes altering image values assigned to the volume elements in the outer layer.

13. The method of claim 11, wherein creating the smaller 3D surface includes forming a 3D surface around the volumetric image model after removing the outer layer of volume elements.

14. The method of claim 5, wherein creating the smaller 3D surface includes creating a copy of the 3D surface model of the dentition and reducing the size of the copy.

15. The method of claim 14, wherein reducing the size of the copy of the 3D surface model includes selecting points on the 3D surface model and moving the points toward an inner portion of the 3D surface model.

16. The method of claim 15, wherein each of the points is a vertex on a 3D surface triangle.

17. The method of claim 16, wherein moving the points includes, for each point, calculating normals for the triangles that share the point, averaging the normals to create an averaged normal, and moving the point along the averaged normal.

18. The method of claim 15, further comprising placing mathematical springs between adjacent pairs of the points before moving the points.

19. A computer program, stored on a tangible storage medium, for use in producing a positive mold of an orthodontic appliance, the program comprising executable instructions that, when executed by a computer, cause the computer to:
obtain a digital dentition model that defines the shape of an orthodontic appliance;
alter the digital dentition model to remove a portion that does not affect the shape of the orthodontic appliance; and
use the altered digital dentition model to construct a positive mold for the orthodontic appliance.

20. The program of claim 19, wherein, in using the altered digital dentition model to construct a positive mold for the orthodontic appliance, the computer delivers the altered digital dentition model to a rapid prototyping system.

21. The program of claim 20, wherein, in delivering the altered digital dentition model to a rapid prototyping system, the computer delivers a volumetric image model to a stereolithography machine.

22. The program of claim 20, wherein, in delivering the altered digital dentition model to a rapid prototyping system, the computer delivers data identifying boundaries of a surface model of the dentition.

23. The program of claim 19, wherein the digital dentition model includes a 3D surface model of a dentition, and wherein, in altering the digital dentition model, the computer:
creates another 3D surface model that is smaller than the 3D surface model of the dentition;
defines a cutting surface that intersects both the 3D surface model of the dentition and the smaller 3D surface model; and
performs a cut operation along the cutting surface to form a single 3D surface model that follows contours of both the 3D surface model of the dentition and the smaller 3D surface model.

24. The program of claim 23, wherein, in forming the single 3D surface model, the computer forms a shell having an outer surface that follows contours of the 3D surface model of the dentition and having an inner surface that follows contours of the smaller 3D surface model.

25. The program of claim 24, wherein, in creating the smaller 3D surface model, the computer identifies an area that defines a cavity in the shell and forms the smaller 3D surface around the cavity.

26. The program of claim 23, wherein, in using the altered digital dentition model to construct a positive mold for the orthodontic appliance, the computer delivers a data set that identifies boundaries of the single 3D surface model to a rapid prototyping system.

27. The program of claim 26, wherein, in delivering a data set to a rapid prototyping system, the computer delivers a volumetric image model of the single 3D surface model to a stereolithography machine.

28. The program of claim 23, wherein the computer creates a volumetric image model of the dentition from the 3D surface model of the dentition.

29. The program of claim 28, wherein, in creating the smaller 3D surface model, the computer removes an outer layer of volume elements from the volumetric image model.

30. The program of claim 29, wherein, in removing the outer layer of volume elements, the computer alters image values assigned to the volume elements in the outer layer.

31. The program of claim 29, wherein, in creating the smaller 3D surface, the computer forms a 3D surface around the volumetric image model after removing the outer layer of volume elements.

32. The program of claim 23, wherein, in creating the smaller 3D surface, the computer creates a copy of the 3D surface model of the dentition and reduces the size of the copy.

33. The program of claim 32, wherein, in reducing the size of the copy of the 3D surface model, the computer selects points on the 3D surface model and moves the points toward an inner portion of the 3D surface model.

34. The program of claim 33, wherein each of the points is a vertex on a 3D surface triangle.

35. The program of claim 34, wherein, in moving the points, the computer, for each point, calculates normals for the triangles that share the point, averages the normals to create an averaged normal, and moves the point along the averaged normal.

36. The program of claim 33, wherein the computer also places mathematical springs between adjacent pairs of the points before moving the points.

37. A system for use in producing a positive mold of an orthodontic appliance, the system comprising:
    processing circuitry configured to obtain a digital dentition model that defines the shape of an orthodontic appliance and alter the digital dentition model to remove a portion that does not affect the shape of the orthodontic appliance; and
    a mold producing system configured to receive the altered digital dentition model from the programmable processing device and construct a positive mold for the orthodontic appliance.

38. The system of claim 37, wherein the mold producing system includes a rapid prototyping system.

39. The system of claim 38, wherein the rapid prototyping system includes a stereolithography machine.

40. The system of claim 37, wherein the altered digital dentition model received by the mold producing system includes data identifying boundaries of a surface model of the dentition.

41. The system of claim 37, wherein the altered digital dentition model received by the mold producing system includes a 3D volumetric image model of the dentition.

42. The system of claim 37, wherein the digital dentition model includes a 3D surface model of a dentition, and wherein the processing circuitry is configured to:
    create another 3D surface model that is smaller than the 3D surface model of the dentition;
    define a cutting surface that intersects both the 3D surface model of the dentition and the smaller 3D surface model; and
    perform a cut operation along the cutting surface to form a single 3D surface model that follows contours of both the 3D surface model of the dentition and the smaller 3D surface model.

43. The system of claim 42, wherein the processing circuitry is configured to form a shell having an outer surface that follows contours of the 3D surface model of the dentition and having an inner surface that follows contours of the smaller 3D surface model.

44. The system of claim 43, wherein the processing circuitry is configured to identify an area that defines a cavity in the shell and form the smaller 3D surface around the cavity.

45. The system of claim 42, wherein the processing circuitry is configured to deliver a data set that identifies boundaries of the single 3D surface model to a rapid prototyping system.

46. The system of claim 45, wherein the processing circuitry is configured to deliver a volumetric image model of the single 3D surface model to a stereolithography machine.

47. The system of claim 42, wherein the processing circuitry is configured to create a volumetric image model of the dentition from the 3D surface model of the dentition.

48. The system of claim 47, wherein the processing circuitry is configured to remove an outer layer of volume elements from the volumetric image model.

49. The system of claim 48, wherein the processing circuitry is configured to alter image values assigned to the volume elements in the outer layer.

50. The system of claim 48, wherein the processing circuitry is configured to form a 3D surface around the volumetric image model after removing the outer layer of volume elements.

51. The system of claim 42, wherein the processing circuitry is configured to create a copy of the 3D surface model of the dentition and reduce the size of the copy.

52. The system of claim 51, wherein the processing circuitry is configured to select points on the 3D surface model and move the points toward an inner portion of the 3D surface model.

53. The system of claim 52, wherein each of the points is a vertex on a 3D surface triangle.

54. The system of claim 53, wherein the processing circuitry is configured, for each point, to calculate normals for the triangles that share the point, average the normals to create an averaged normal, and move the point along the averaged normal.

55. The system of claim 52, wherein the processing circuitry is configured to place mathematical springs between adjacent pairs of the points before moving the points.

* * * * *